United States Patent
Bae et al.

(10) Patent No.: US 10,888,663 B2
(45) Date of Patent: Jan. 12, 2021

(54) TITANUM FILTER FOR SYRINGES AND ITS MANUFACTURING METHOD

(71) Applicant: HANATECH CO., LTD., Gimpo-si (KR)

(72) Inventors: Chang Hwan Bae, Seoul (KR); Gun Suk In, Incheon (KR); Hong Jin Kim, Seoul (KR); Kwon Ung Hwang, Gimpo-si (KR)

(73) Assignee: HANATECH CO., LTD., Gimpo-si (KR)

( * ) Notice: Subject to any disclaimer, the term of this patent is extended or adjusted under 35 U.S.C. 154(b) by 0 days.

(21) Appl. No.: 16/539,381

(22) Filed: Aug. 13, 2019

(65) Prior Publication Data

US 2020/0046903 A1 Feb. 13, 2020

(30) Foreign Application Priority Data

Aug. 13, 2018 (KR) .................. 10-2018-0094568

(51) Int. Cl.
*A61M 5/31* (2006.01)
*A61M 5/165* (2006.01)
*B01D 39/20* (2006.01)

(52) U.S. Cl.
CPC .......... *A61M 5/3145* (2013.01); *A61M 5/165* (2013.01); *B01D 39/2034* (2013.01)

(58) Field of Classification Search
CPC ................ A61M 5/3145; A61M 5/165; A61M 2207/00; A61M 2205/75; A61M 2205/02; B01D 39/2034; B01D 39/2031; B22F 3/12; B22F 3/24; B22F 5/106; B22F 2003/247
See application file for complete search history.

(56) References Cited

FOREIGN PATENT DOCUMENTS

| JP | 2002066229 A | | 3/2002 |
| JP | 2011177661 A | * | 9/2011 |
| JP | 2011177661 A | | 9/2011 |
| KR | 101719506 B1 | * | 3/2017 |
| KR | 101719506 B1 | | 3/2017 |

* cited by examiner

*Primary Examiner* — Jessee R Roe
*Assistant Examiner* — Rebecca Janssen
(74) *Attorney, Agent, or Firm* — Novick, Kim & Lee, PLLC; Jae Youn Kim; Jihun Kim

(57) ABSTRACT

Provided is a titanium filter for syringes and its manufacturing method, more particularly, a titanium filter for syringes which has an improved filtering power and high safety and its manufacturing method. The titanium filter for syringes comprises: a first body having a hollow hole formed on the inner side thereof; and a second body configured to extend in the longitudinal direction of the first body and to cover one side of the hollow hole, wherein the first body and the second body are composed of titanium powders.

6 Claims, 4 Drawing Sheets

TITANUM FILTER FOR SYRINGES AND ITS MANUFACTURING METHOD

BACKGROUND OF THE INVENTION

Field of the Invention

The present invention relates to a titanium filter for syringes and its manufacturing method, more particularly, to a titanium filter for syringes which has an improved filtering power and high safety and its manufacturing method.

Description of the Related Art

Generally, in most cases, disposable syringes are used for medicine administration to infected patients in order to prevent secondary infections caused by the injection process. The disposable syringes inject a mixture of a liquid medicine in the form of a solution and powders or a liquid medicine in the form of a solution alone. The liquid medicines are mostly contained in an ampule made of glass or plastics in order to prevent contamination during storage and transportation.

An injection opening is made on the ampoule by breaking a part of the top thereof, or an injection needle is injected into the rubber stopper of the ample to take in the liquid medicine.

However, during this process, foreign substances such as fine glass powders or rubber pieces are mixed with the liquid medicine and introduced into the syringe along with the liquid medicine, and the introduced foreign substances are administered into the patient along with the liquid medicine. Therefore, it is preferable to use a filter mounted into the injection needle to prevent the administration of foreign substances to patients.

However, in the case where a filter is mounted into the injection needle as described above, if the filtering power of the filter is increased, the rate at which the syringe administers a liquid medicine decreases, and if the filter is manufactured such that the rate at which the syringe administers a liquid medicine increases, the filtering power of the filter is deteriorated. Thus, there is a need for a manufacturing method of a titanium filter for syringes that allows rapid administration while preventing deterioration of the filtering performance against foreign substances.

Also, when a liquid medicine has a high viscosity, an injection of the liquid medicine can be injected only when the injection pressure is high. In this regard, in general membrane type filters, a high injection pressure may result in increased filter pore sizes, leading to deteriorated filtering performance. However, in titanium filters, the filtering performance is not deteriorated even at a high injection pressure, due to the bonding between metals. Meanwhile, in practice, a liquid medicine may be injected into a syringe in advance to prepare for emergency patients, etc. In such cases, filters may cause a chemical reaction with the liquid medicine. Also, filters for Ringer syringes may cause a chemical reaction with the liquid medicine because they are used for a long time unlike filters for general syringes. For example, filters may react with the liquid medicine to generate rust. Therefore, there is a need for a manufacturing method of a titanium filter for syringes that prevents a chemical reaction between the filter and a liquid medicine even when the liquid medicine is injected into the syringes in advance.

SUMMARY OF THE INVENTION

An object of the present invention is to provide a titanium filter for syringes which has an improved filtering power and high safety and its manufacturing method.

Objects of the present invention are not limited to the objects described above, and other objects that are not described will be clearly understood by a person skilled in the art from the description below.

In order to achieve the above objectives, an embodiment of the present invention provides a titanium filter for syringes, comprising: a first body having a hollow hole formed on the inner side thereof; and a second body configured to extend in the longitudinal direction of the first body and to cover one side of the hollow hole, wherein the first body and the second body are composed of titanium powders.

In an embodiment of the present invention, the titanium powders have a composition ratio of irregular square powders:spherical powders of 70 to 90%:10 to 30%.

Also, the titanium powders may be a mixture of irregular square powders and spherical powders at an appropriate ratio to ensure Green strength and obtain the required filtering power after sintering. Specifically, the titanium powders may be a mixture of 37 to 67% of square powders with a particle size of 75 μm to 150 μm, 14 to 44% of square powders with a particle size of 0 μm to 75 μm and 5 to 30% of spherical powders with a particle size of 0 μm to 75 μm.

In an embodiment of the present invention, the titanium powders may be alloy powders composed of, by weight, 0 to 0.4% of oxygen (O), 0 to 0.04% of nitrogen (N), 0 to 0.03% of hydrogen (H), 0 to 0.04% of carbon (C), 0 to up to 0.05% of chlorine (Cl), 0 to 0.05% of iron (Fe), 0 to 0.03% of silicon (Si) and the balance of titanium (Ti), based on the total weight of the titanium powders.

In an embodiment of the present invention, in the case of the filter for injections, the inner diameter of the hollow hole is 1.15 mm to 1.25 mm, the thickness of the first body is 0.71 mm to 0.72 mm, and the thickness of the second body is 0.75 mm to 0.85 mm, and in the case of the filter for Ringer solutions, the inner diameter of the hollow hole is 3.2 mm to 3.6 mm, the thickness of the first body is 0.80 to 0.82 mm, and the thickness of the second body is 0.80 mm to 0.82 mm.

In order to achieve the above objectives, an embodiment of the present invention provides a manufacturing method of a titanium filter for syringes, comprising the steps of: a) mixing titanium powders and a molding lubricant to form a mixture; b) charging the mixture into a mold and applying a molding pressure to form a molded body; c) degreasing the molded body which has been formed; and d) sintering the degreased product, which has been degreased, under vacuum to form a titanium filter.

In an embodiment of the present invention, in step a), the titanium powders may be alloy powders composed of, by weight, 0 to 0.4% of oxygen (O), 0 to 0.04% of nitrogen (N), 0 to 0.03% of hydrogen (H), 0 to 0.04% of carbon (C), 0 to up to 0.05% of chlorine (Cl), 0 to 0.05% of iron (Fe), 0 to 0.03% of silicon (Si) and the balance of titanium (Ti), based on the total weight of the titanium powders.

In an embodiment of the present invention, in step a), the molding lubricant may be included in an amount of 0.3 to 1.0 part by weight based on 100 parts by weight of the titanium powders.

In an embodiment of the present invention, in step c), the molded body may be degreased in a vacuum furnace at a degreasing temperature of 300° C. to 700° C. under the degree of vacuum of $10^{-2}$ Torr or less for 20 to 60 minutes.

In an embodiment of the present invention, in step d), the molded body may be sintered under vacuum at a temperature of 1120° C. to 1160° C. for 30 to 60 minutes.

In an embodiment of the present invention, in step d), the molded body may be sintered under vacuum at a vacuum pressure of $10^{-3}$ Torr to $10^{-6}$ Torr.

In an embodiment of the present invention, the method may further comprise, after step d), the step of selecting a titanium filter.

Also, in an embodiment, the present invention provides a manufacturing method of a metal filter for syringes, comprising the steps of: a) mixing metal powders and a molding lubricant to form a mixture; b) charging the mixture into a mold and applying a molding pressure to form a molded body; c) sintering the molded body to form a sintered body; and d) subjecting the sintered body to vacuum heat treatment to form a metal filter.

In an embodiment of the present invention, in step a), the metal powders may be alloy powders composed of, by weight, greater than 0 and not greater than 0.030% of carbon (C), greater than 0 and not greater than 0.015% of sulfur (S), 2.0 to 3.0% of molybdenum (Mo), 12.0 to 14.0% of nickel (Ni), greater than 0 and not greater than 0.2% of manganese (Mn), 16.0 to 18.0% of chromium (Cr), 0.5 to 1.0% of silicon (Si), and the balance of iron (Fe), based on the total weight of the metal powders.

In an embodiment of the present invention, in step a), the molding lubricant may be included in an amount of 0.5 to 1.5 parts by weight based on 100 parts by weight of the metal powders.

In an embodiment of the present invention, in step a), the metal powders may be powders manufactured by a high-pressure water spraying method and have an irregular shape. Also, the metal powders may be composed of 40 to 70% of powders with a particle size of 140 mesh to less than 200 mesh, 20 to 55% of powders with a particle size of 200 mesh to less than 270 mesh, and greater than 0 to 5% of powders with a particle size of 270 mesh or more.

In an embodiment of the present invention, in step b), the molding pressure may be a press pressure of 2 ton/cm$^2$ to 5 ton/cm$^2$.

In an embodiment of the present invention, the method may further comprise, before step c), the step of preheating the sintered body at a temperature of 400° C. to 900° C.

In an embodiment of the present invention, in step c), the molded body may be sintered at a temperature of 1100° C. to 1200° C. for 25 to 45 minutes.

In an embodiment of the present invention, the method may further comprise, after step (c), the step of cooling the sintered body in a sintering furnace.

In an embodiment of the present invention, in step d), the sintered body may be subjected to vacuum heat treatment at a temperature of 1100° C. to 1200° C., and subjected to gas cooling at a rate of 0.4 to 1.0° C./sec for 20 to 60 minutes.

In an embodiment of the present invention, the metal filter formed after step d) may have a density of 5.2 g/cm$^3$ to 5.8 g/cm$^3$.

DETAILED DESCRIPTION OF THE PREFERRED EMBODIMENTS

Figure 1:
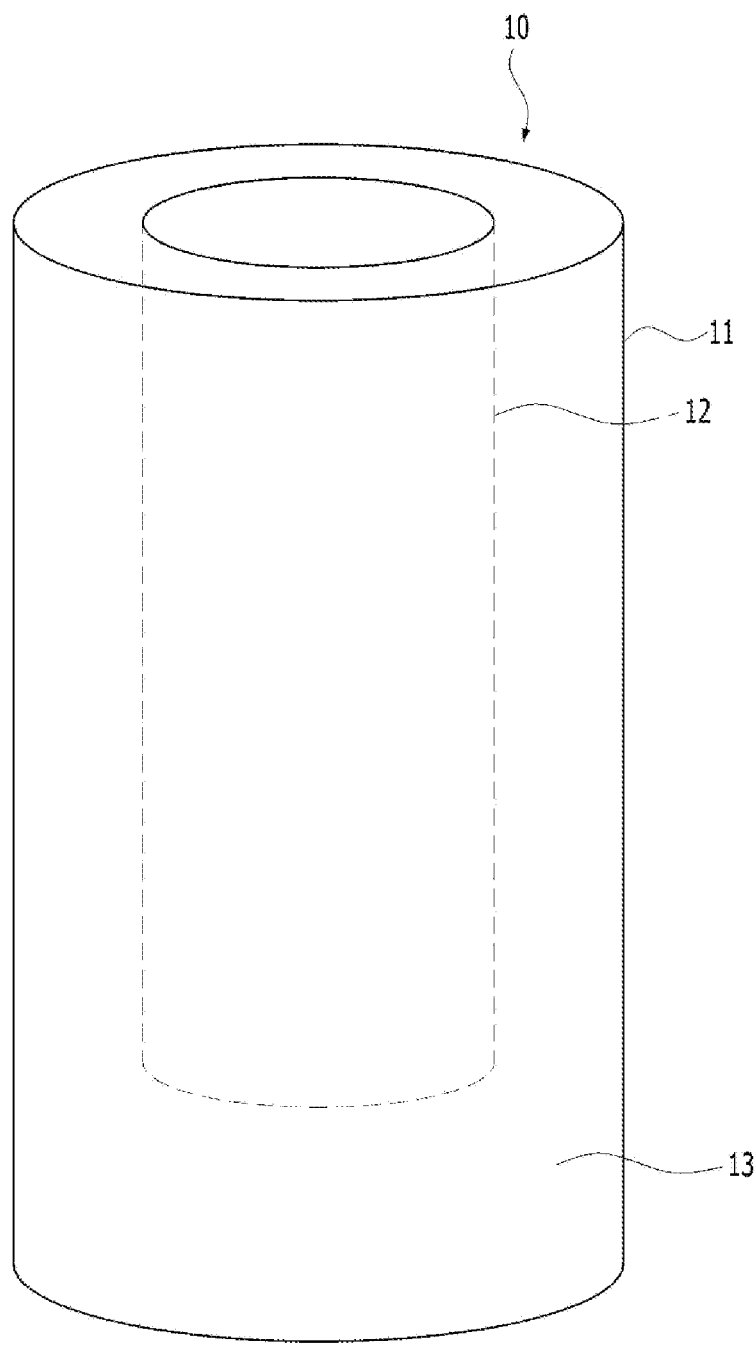
FIG. 1 is a perspective view of a titanium filter for syringes according to an embodiment of the present invention.

Hereinafter, the present invention will be described with reference to the accompanying drawings. The present invention may, however, be embodied in many different forms and should not be construed as limited to the embodiments set forth herein. In order to clearly illustrate the present invention, parts not related to the description are omitted, and like parts are denoted by like reference numerals throughout the specification.

Herein, when a part is described as being "connected" or "coupled" to another part, it may be directly connected or coupled to another part or may be indirectly connected or coupled to another part with a member interposed therebetween. Also, the terms "comprise" and "include" as used herein refer to the presence of the corresponding component and is not intended to exclude additional components, unless otherwise specified.

The terms as used herein are for the purpose of describing particular embodiments only and is not intended to limit the invention. As used herein, the singular forms "a," "an" and "the" are intended to include the plural forms as well, unless the context clearly indicates otherwise. It is to be further understood that the terms "comprise," "include" and "have" as used herein specify the presence of stated features, numbers, steps, actions, components, parts, or a combination thereof, but do not preclude the presence or addition of one or more other features, numbers, steps, actions, components, parts, or a combination thereof.

Hereinafter, the present invention will be described in detail with reference to the accompanying drawings.

Figure 2:
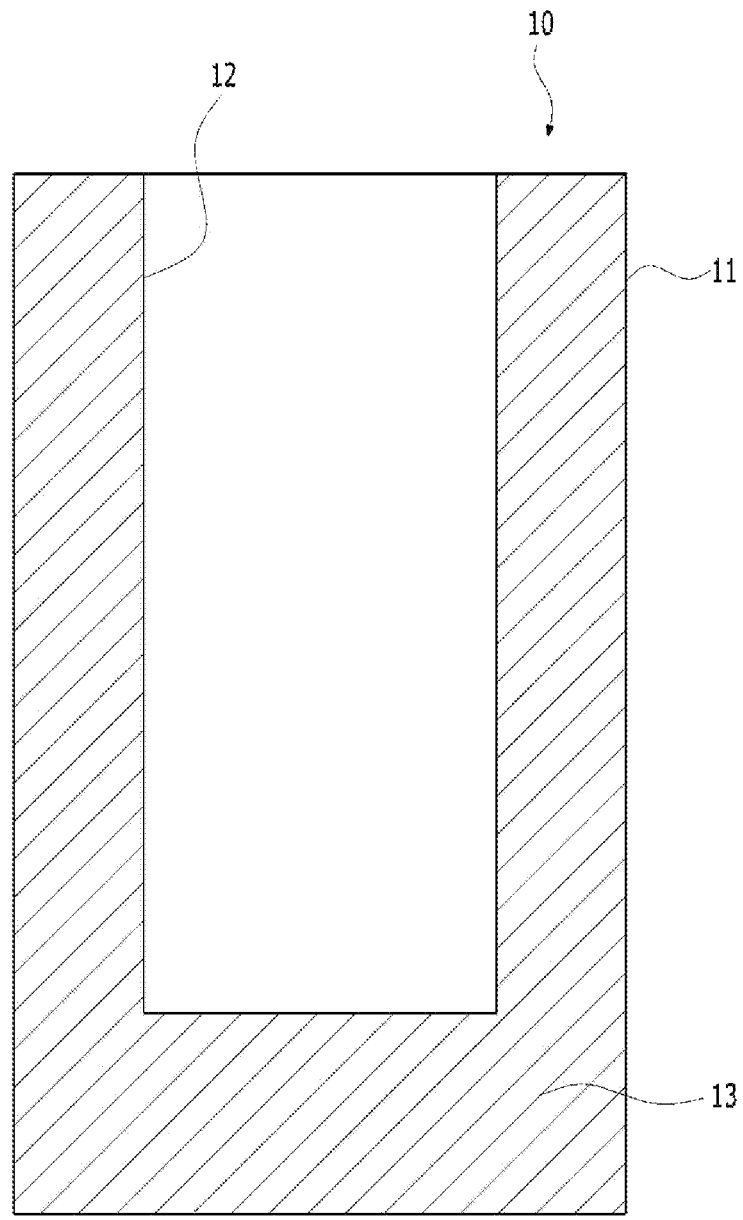
FIG. 2 is a longitudinal sectional view of a titanium filter for syringes according to an embodiment of the present invention.

FIG. 1 is a perspective view of a titanium filter for syringes according to an embodiment of the present invention, and FIG. 2 is a longitudinal sectional view of a titanium filter for syringes according to an embodiment of the present invention.

As shown in FIG. 1 and FIG. 2, the titanium filter 10 for syringes manufactured by the manufacturing method of a titanium filter for syringes comprise a first body 11 and a second body 13.

Specifically, the first body 11 may be configured to have a cylindrical shape, and have a hollow hole 12 formed on the inner side thereof. Here, the diameter of the hollow hole 12 may be 1.15 mm to 1.25 mm. The appearance of the first body 11 is not limited to this embodiment.

The second body 13 may be configured to extend in the longitudinal direction of the first body 11 and to cover one side of the hollow hole 12. Also, the thickness of the second body 13 may be 0.75 mm to 0.85 mm.

Here, the thickness of the second body 13 may be 0.71 mm to 0.72 mm. Also, the titanium filter 10 for syringes may be configured to have a breaking strength of 30 kgf or more.

In the case of the filter for Ringer solutions, the inner diameter of the hollow hole of may be 3.2 mm to 3.6 mm, the thickness of the first body may be 0.8 mm to 0.82 mm, and the thickness of the second body may be 0.8 mm to 0.82 mm.

However, the dimensions of the hollow hole 12, the first body 11, and the second body 13 of the titanium filter for syringes are not limited thereto, and may vary.

The shape of the titanium filter 10 for syringes may be configured to have a square pillar shape or a plate shape.

The titanium filter 10 for syringes configured to have such a shape allows to administer a liquid medicine to a patient at a rate at which foreign substances contained in the liquid medicine can be filtered.

In particular, according to an embodiment of the present invention, the titanium filter 10 for syringes may make it possible for the administration of a 10 cc dose of a liquid medicine at a common injection pressure by a syringe commonly used in the art to take 4 to 25 seconds. If it takes less than 4 seconds for a syringe to administer a liquid medicine, foreign substances contained in the liquid medicine may not be completely filtered.

On the other hand, if the time for administration is longer than 25 seconds, the time required for administration of a liquid medicine is excessively long, which is not efficient. Therefore, when a 10 cc dose of a liquid medicine is administered by a syringe, it is preferable that the administration of the liquid medicine take 4 to 25 seconds.

The rate of administration of a liquid medicine by the titanium filter 10 for syringes can be controlled by changing the surface area of the titanium filter 10 for syringes. Specifically, it is possible to increase the rate of administration of a liquid medicine by increasing the surface area of the titanium filter 10 for syringes, and it is possible to decrease the rate of administration of a liquid medicine by decreasing the surface area of the titanium filter 10 for syringes.

Also, the first body 11 and the second body 12 may be composed of titanium powders. Specifically, the titanium powders may be alloy powders composed of, by weight, 0 to 0.4% of oxygen (O), 0 to 0.04% of nitrogen (N), 0 to 0.03% of hydrogen (H), 0 to 0.04% of carbon (C), 0 to up to 0.05% of chlorine (Cl), 0 to 0.05% of iron (Fe), 0 to 0.03% of silicon (Si) and the balance of titanium (Ti).

When the oxygen content exceeds 0.40 wt %, sintering bonding may not occur. Therefore, preferably, oxygen is limited to 0 to 0.40 wt %.

When the nitrogen content exceeds 0.04 wt %, the strength becomes high, but brittleness may occur.

When the carbon content exceeds 0.04 wt %, corrosion resistance may be deteriorated. Thus, it is preferable to minimize the carbon content.

The iron content should be controlled to be less than 0.05 wt %. When it exceeds the value, corrosion resistance may be deteriorated. Thus, it is preferable to minimize the iron content.

The silicon content should be controlled to be less than 0.03 wt %. When it exceeds the value, the strength of the powder particles increases, resulting in a low Green strength. Thus, it is preferable to minimize the silicon content.

Incidentally, most of the titanium powders have an irregular shape, and spherical fine powders are added to help to form pores. The powders of an irregular shape are a mixture of small and large particles at an appropriate ratio, thus obtaining the fluidity of the powders to achieve a uniform density during molding, and also ensuring an appropriate Green strength after molding. The spherical powders allow to obtain a good fluidity. Also, as small spherical powders are used, it is easy to obtain small pores.

Specifically, the titanium powders have a composition ratio of irregular square powders:spherical powders of 70 to 90%:10 to 30%.

More specifically, the titanium powders may be a mixture of irregular square powders and spherical powders at an appropriate ratio to ensure Green strength and obtain the required filtering power after sintering. Specifically, the titanium powders may be a mixture of 37 to 67% of square powders with a particle size of 75 μm to 150 μm, 14 to 44% of square powders with a particle size of 0 μm to 75 μm, and 5 to 30% of spherical powders with a particle size of 0 μm to 75 μm.

The titanium powders, which have such an irregular shape, allow the titanium filter 10 for syringes to have a filtering power capable of filtering out at least 90% of foreign substances with a size of 0.005 mm, and also to have an appropriate particle size such that it takes 25 seconds or less for a syringe to administer 10 cc of a liquid medicine.

A molding lubricant may be added to the process of manufacturing the titanium filter 10 for syringes. The molding lubricant may be included in an amount of 0.3 to 1.0 part by weight based on 100 parts by weight of the titanium powders.

In an embodiment, Kenolube may be used as the molding lubricant. However, the type of the molding lubricant is not limited thereto, and zinc stearate and amide wax may also be used. During molding, titanium powders in the mold are compressed to cause friction against the mold surface. At this time, heat may be generated along with scratches on the mold surface. The molding lubricant is used to prevent these.

However, when the amount of the molding lubricant added exceeds 1.0 wt %, the compressibility may be deteriorated, burn-out may occur during sintering, resulting in defects in the molded body, and the molding lubricant may remain in oxidized form on the surface of the titanium filter 10 for syringes as a partly manufactured product. On the other hand, when the molding lubricant is used in an amount less than 0.3 wt %, it may cause generation of heat and scratches on the mold surface, which may be unsuitable for use. Therefore, preferably, the molding lubricant is included in an amount of 0.3 to 1.0 part by weight based on 100 parts by weight of the titanium powders.

Also, the molding lubricants added may be completely removed in the degreasing step.

As described above, the titanium filter 10 for syringes, composed of titanium powders, is porous so that it can filter foreign substances contained in a liquid medicine. Also, as described above, when a liquid medicine is administered to a patient, the titanium filter 10 for syringes allows to give an injection to the patient promptly while filtering the foreign substances contained in the liquid medicine.

Hereinafter, a manufacturing method of the aforementioned titanium filter 10 for syringes will be described with reference to the following drawings.

Figure 3:
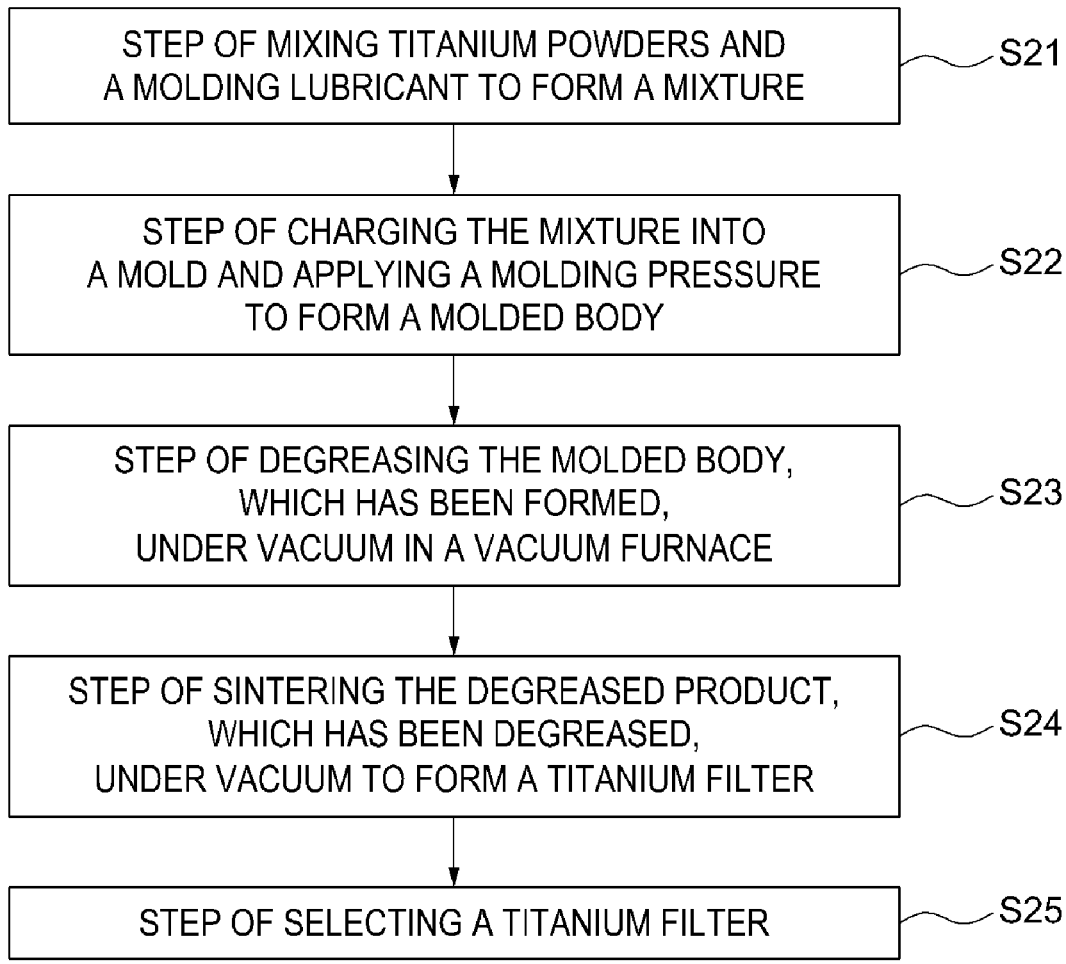
FIG. 3 is a flowchart of a manufacturing method of a titanium filter for syringes according to an embodiment of the present invention.

FIG. 3 is a flowchart of a manufacturing method of a titanium filter for syringes according to an embodiment of the present invention.

With reference to FIG. 3, the manufacturing method of a titanium filter for syringes comprises the step (S21) of mixing titanium powders and a molding lubricant to form a mixture. Specifically, the titanium powders and molding lubricant in the step (S21) of mixing titanium powders and a molding lubricant to form a mixture are the same as described above, and thus, a detailed description thereof will be omitted. The titanium powders and molding lubricant configured as described above may be charged into a mixer and mixed therein, and the mixing time may be 20 to 40 minutes.

The manufacturing method of a titanium filter for syringes may comprise, after the step (S21) of mixing titanium powders and a molding lubricant to form a mixture, the step (S22) of charging the mixture into a mold and applying a molding pressure to form a molded body.

Specifically, the step (S22) of charging the mixture into a mold and applying a molding pressure to form a molded body is a step of charging the mixture formed in the step (S21) of mixing titanium powders and a molding lubricant to form a mixture into a mold and applying a molding pressure to form a molded body Here, the molding pressure may be a pressure of 2 ton/cm$^2$ to 6 ton/cm$^2$. When the pressure is less than 2 ton/cm$^2$, the molded body may not be formed in a predetermined shape, and also the compressed density may decrease, so that the titanium filter 10 for syringes as a final product may have a larger pore size, resulting in deteriorated filtering performance. On the other hand, when the pressure exceeds 6 ton/cm$^2$, the density of the molded body may increase, so that the porosity may decrease, leading to a problem that the time for administration of a liquid medicine by a syringe becomes longer. Therefore, preferably, the molding pressure is limited to a range of 2 ton/cm$^2$ to 6 ton/cm$^2$. Also, the step (S22) of charging the mixture into a mold and applying a molding pressure to form a molded body may further comprise the step of checking for powders attached to the molded body and injecting air to remove the powders.

The density of the molded body formed in the step (S22) of charging the mixture into a mold and applying a molding pressure to form a molded body may be 2.5 g/cm$^3$ to 4.0 g/cm$^3$.

The manufacturing method of a titanium filter for syringes may comprise, after the step (S22) of charging the mixture into a mold and applying a molding pressure to form a molded body, the step (S23) of degreasing the molded body.

In the step (S23) of degreasing the molded body, the molded body may be degreased by vacuum heat treatment at a temperature of 300° C. to 700° C. for 20 to 60 minutes. In the step (S23) of degreasing the molded body which has been formed, the molding lubricants contained in the molded body may be completely burned and removed.

When the degreasing temperature of the molded body is less than 300° C., the molding lubricant may not be removed. In addition, when the degreasing temperature of the molded body is higher than 700° C. or when the degreasing time is long, it may consume more energy than the energy required for degreasing, resulting in waste of energy.

Also, when the heating time of the molded body is less than 20 minutes, sufficient heating may not be performed, so that the molding lubricants may not be completely removed. Also, when the heating time of the molded body is 60 minutes, it is enough to completely remove the molding lubricants. Therefore, when the heating time of the molded body exceeds 60 minutes, it may lead to consumption of more energy than necessary.

Therefore, it is preferable that the molded body be degreased in a vacuum sintering furnace at a temperature of 300° C. to 700° C. for 20 to 60 minutes.

After the step (S23) of degreasing the molded body, the step (S24) of sintering the molded body under vacuum to form a titanium filter may be performed.

The step (S24) of sintering the molded body under vacuum to form a titanium filter is a step of applying heat to the degreased product to allow sufficient bonding between the particles constituting the degreased product and thereby to improve the bonding force between the particles. In particular, the degreased product may be sintered under vacuum at a temperature of 1120° C. to 1160° C. for 30 to 60 minutes.

When the sintering temperature is less than 1100° C., the sintering temperature is too low to achieve proper sintering, so that the strength may be deteriorated. When the sintering temperature is less than 1120° C., the density of the material may decrease, the pore size may become large, leading to deteriorated filtering performance against foreign substances, and the corrosion resistance may decrease, leading to corrosion.

On the other hand, when the molded body is subjected to vacuum heat treatment at a temperature exceeding 1160° C., the shape of the titanium filter 10 for syringes may be deformed, and in particular, the flow rate may be lowered down due to decreased porosity, leading to low practicability. That is, when the molded body is subjected to vacuum heat treatment at a temperature exceeding 1160° C., the desired filtering power and flow rate cannot be obtained, and the dimensional precision may decrease, leading to low assembling performance between a syringe and the titanium filter 10 for syringes. Also, when the sintering time is less than 30 minutes, sintering is not sufficiently performed, leading to a decreased filtering power. When the sintering time exceeds 60 minutes, the strength increases, but the dimensional precision may be lowered due to sintering deformation.

Also, the sintered body may be sintered under vacuum under a vacuum pressure of $10^{-3}$ Torr to $10^{-6}$ Torr.

Here, the heat treatment using vacuum involves a less amount of gases containing impurities such as oxygen, carbon dioxide, and carbon monoxide, thus preventing a surface reaction such as oxidation and carburization from occurring in the molded body, reducing the oxide film on the powder particle surfaces, and allowing intergranular sintering bonding. In addition, it can remove, through thermal decomposition or reduction, contaminants on the surface such as remnants of the molding lubricant used in the process of manufacturing the titanium filter 10 for syringes. That is, the titanium filter 10 for syringes that went through vacuum heat treatment can prevent transformation of the chemical ingredients of the materials and maintain a clean surface. In addition, the surface of the titanium filter 10 for syringes is kept clean even after vacuum heat treatment. Thus, the filter does not require post-treatment after the vacuum heat treatment, and thus is economical.

The step (S24) of sintering the molded body, which has been degreased, under vacuum to form a titanium filter may further comprise the step of cooling the molded body in a sintering furnace. The sintered body that has been sintered may be cooled in the sintering furnace using a water jacket. Here, the sintered body may be cooled by water cooling. However, the cooling method of the molded body is not limited to the water cooling according to this embodiment.

In an embodiment, the sintered body that has undergone vacuum heat treatment may be cooled using an inert gas (such as Ar).

When a liquid medicine is administered to the body of a patient, it is generally preferable that at least 90% of the foreign substances be filtered. The titanium filter 10 for syringes manufactured by the aforementioned method is designed to have a uniform pore size and an optimized thickness of the second body 13, and thus can filter at least 90% of the foreign substances contained in a liquid medicine.

Also, in particular, the titanium filter 10 for syringes formed by the aforementioned method is subjected to vacuum heat treatment so that it will have a density of 2.5 g/cm$^3$ of 4.0 g/cm$^3$.

When the density of the titanium filter 10 for syringes that has undergone vacuum heat treatment is less than 2.5 g/cm$^3$, the porosity increases, which shortens the time for administering a liquid medicine, but the filtering power may decrease.

Conversely, when the density of the titanium filter 10 for syringes exceeds 4.0 g/cm$^3$, the filtering power increases, but the time for administering a liquid medicine increases excessively, which is not efficient.

Therefore, when the density of the titanium filter 10 for syringes is 2.5 g/cm$^3$ to 4.0 g/cm$^3$, the time for administering a liquid medicine is 4 to 25 seconds, and the filter can filter at least 90% of the foreign substances contained in a liquid medicine, which is most suitable.

Hereinafter, specific experimental examples for the step (S24) of sintering the molded body under vacuum to form a titanium filter will be described.

Example 1

In Example 1, titanium powders composed of, by weight, 0.4% of oxygen (O), 0.04% of nitrogen (N), 0.03% of hydrogen (H), 0.04% of carbon (C), 0.05% of chlorine (Cl), 0.05% of iron (Fe), 0.03% of silicon (Si) and the balance of titanium (Ti) were mixed with 0.8 part by weight of a molding lubricant based on 100 parts by weight of the titanium powders for 25 minutes to form a mixture. A molding pressure of 3.4 ton/cm$^2$ was applied to the mixture to form a molded body. Then, the molded body was degreased at a temperature of 450° C. in a vacuum furnace atmosphere of 10$^{-2}$ Torr for 40 minutes. Then, the degreased product was sintered under vacuum under the degree of vacuum of 10$^{-4}$ Torr at a temperature of 1120° C. for 60 minutes to obtain a titanium filter.

Example 2

In Example 2, a titanium filter was manufactured by controlling the vacuum sintering temperature at 1160° C., and keeping the remaining process parameters identical to those of Example 1.

Comparative Example 1

In Comparative Example 1, a titanium filter was manufactured by controlling the vacuum sintering temperature at 1100° C., and keeping the remaining process parameters identical to those of Example 1.

Comparative Example 2

In Comparative Example 2, a titanium filter was manufactured by controlling the vacuum sintering temperature at 1200° C., and keeping the remaining process parameters identical to those of Example 1.

Experimental Method

Measurements were made for the time required to administer 10 cc of a liquid medicine at a normal injection pressure after a titanium filter is mounted into a syringe, and its filtering power against foreign substances. Here, comparison was made between the foreign substances contained in the liquid medicine in an ampoule and the foreign substances contained in the liquid medicine discharged through the titanium filter. The filtering power is the reduction rate of foreign substances expressed in percentage.

TABLE 1

| Classification | Sintering temperature (° C.) | Time required (sec) | Filtering power (%) | Corrosion resistance |
|---|---|---|---|---|
| Example 1 | 1120 | 4 | 95 | Conforming |
| Example 2 | 1160 | 25 | 98 | Conforming |
| Comparative Example 1 | 1100 | 3 | 76 | Non-conforming |
| Comparative Example 2 | 1200 | 45 | 99 | Conforming |

As shown in Table 1 above, in Example 1 of the present invention, it took 4 seconds for the syringe to administer the liquid medicine, and the filtering power against foreign substances was 95%. In Example 2, it took 25 seconds for the syringe to administer the liquid medicine, and the filtering power against foreign substances was 98%. That is, it can be understood that as the temperature of vacuum heat treatment increases, the filtering power against foreign substances increases, and the time required for administration of a liquid medicine increases. Also, it can be seen that the corrosion resistance of Examples 1 and 2 satisfies the criteria and thus is conforming.

In contrast, in Comparative Example 1, although the time required for administration of a liquid medicine was 3 seconds so that the rate of administration of a liquid medicine was higher than those of Examples 1 and 2, the filtering power was merely 76%, which was lower than those of Examples 1 and 2, and the corrosion resistance did not satisfy the criteria and thus was non-conforming. In addition, although Comparative Example 2 achieved a filtering power of 99%, which was similar to that of Example 2, and satisfied the criteria for corrosion resistance, the time required for administration of a liquid medicine in Comparative Example 2 was 45 seconds, and thus the rate of administration of a liquid medicine was significantly low. That is, it can be understood that, when the temperature in the vacuum heat treatment process exceeds 1160° C., the increase in the filtering power becomes small, and the pore size becomes too small, so that the time required for a syringe to administer a liquid medicine greatly increases. Therefore, in the step (S24) of sintering the degreased product, which has been degreased, under vacuum to form a titanium filter, it is preferable to subject the molded body to vacuum heat treatment at a temperature of 1120° C. to 1160° C. so that the titanium filter 10 for syringes will achieve a filtering power of at least 90% while minimizing the time required for a syringe to administer a liquid medicine.

After the step (S24) of sintering the degreased product, which has been degreased, under vacuum to form a titanium filter, the step (S25) of selecting a titanium filter may be performed.

In the step (S25) of selecting a titanium filter, a titanium filter with defects such as discoloration, spots, and cracks may be automatically or visually identified to select a titanium filter without defects.

The titanium filter 10 for syringes configured as described above does not react with an acidic liquid medicine and thus does not discolor or degenerate.

In addition, the titanium filter 10 for syringes manufactured according to the manufacturing method of a titanium filter for syringes is manufactured through vacuum sintering, so that it is possible to prevent rusting resulting from a reaction with a liquid medicine. That is, the titanium filter 10 for syringes can be safely used.

Also, when a liquid medicine has a high viscosity, an injection of the liquid medicine can be injected only when the injection pressure is high. In this regard, general filters are membrane type filters made of a mesh of a resin-based material. If an injection is injected using such a membrane type filter at a high injection pressure, the filter pore sizes may increase, leading to a deteriorated filtering power. In contrast, the titanium filter 10 for syringes according to the present invention is composed of metals formed by intergranular sintering bonding, so that its filter pores are not affected at all by an injection pressure, Thus, its filtering performance is not deteriorated by an injection pressure.

The metal filter for syringes, which is an embodiment of the present invention, are similar in many parts to those of the titanium filter as described above.

As shown in FIG. 1 and FIG. 2, the metal filter 10 for syringes manufactured according to the manufacturing method of a metal filter 10 for syringes comprises a first body 11 and a second body 13. Specifically, the first body 11 may be configured to have a cylindrical shape. Here, the first body 11 may be configured to have a diameter of 2.5 mm to 2.7 mm and a length of 4.5 mm to 5.5 mm. The first body 11 may be configured to have a hollow hole 12 formed on the inner side thereof. Here, the diameter of the hollow hole 12 may be 1.0 mm to 1.4 mm. The length and appearance of the first body 11 is not limited to this embodiment. The second body 13 may be configured to extend in the longitudinal direction of the first body 11 and to cover one side of the hollow hole. Also, the thickness of the second body 13 may be 0.7 mm to 0.9 mm. The metal filter 10 for syringes may be configured to have a density of 5.2 g/cm$^3$ to 5.8 g/cm$^3$. The metal filter 10 for syringes, configured as described above, allows for a syringe to administer a liquid medicine to a patient at a rate at which foreign substances contained in the liquid medicine can be filtered. In particular, according to an embodiment of the present invention, the metal filter 10 for syringes may make it possible for the administration of a 10 cc dose of a liquid medicine at a common injection pressure by a syringe commonly used in the art to take 12 to 25 seconds. If it takes less than 12 seconds for a syringe to administer a liquid medicine, foreign substances contained in the liquid medicine may not be completely filtered. On the other hand, if the time for administration is longer than 25 seconds, the time required for administration of a liquid medicine is excessively long, which is not efficient. Therefore, when a 10 cc dose of a liquid medicine is administered by a syringe, it is preferable that the administration of the liquid medicine take 12 to 25 seconds.

Also, the first body 11 and the second body 12 may be composed of metal powders. Specifically, the metal powders may be alloy powders composed of, by weight, greater than 0 and not greater than 0.030% of carbon (C), greater than 0 and not greater than 0.015% of sulfur (S), 2.0 to 3.0% of molybdenum (Mo), 12.0 to 14.0% of nickel (Ni), greater than 0 and not greater than 0.2% of manganese (Mn), 16.0 to 18.0% of chromium (Cr), 0.5 to 1.0% of silicon (Si), and the balance of iron (Fe), based on the total weight of the metal powders.

Carbon reacts with iron during sintering, thereby improving the strength. However, when the carbon content exceeds 0.030 wt %, the corrosion resistance may be deteriorated. Therefore, it is preferable that the carbon content does not exceed 0.030 wt %.

When the sulfur content exceeds 0.015 wt %, it may combine with manganese to lower the corrosion resistance of the metal filter 10 for syringes. Therefore, it is preferable to limit the sulfur content to 0.015 wt % or less.

Chromium helps to form a passive film, and addition of nickel and molybdenum can further strengthen the passive film to increase the corrosion resistance. However, when the chromium content is out of the range of 16.0% to 18.0%, a passive film may not be properly formed. Also, when the molybdenum content is less than 2.0 or exceeds 3.0%, or when the nickel (Ni) content is less than 12.0% or exceeds 14.0%, the passive film is weakened, leading to deteriorated corrosion resistance. Therefore, it is preferable to limit the chromium content to 16.0% to 18.0%, the molybdenum content to 2.0% to 3.0%, and the nickel content to 12.0% to 14.0%.

When the manganese content exceeds 0.2 wt %, it may combine with sulfur to lower the corrosion resistance of the metal filter (10) for syringes. Therefore, it is preferable to limit the manganese content to 0.2 wt % or less.

When the silicon content is less than 0.5 wt % or exceeds 1.0 wt %, it may lower the corrosion resistance of the metal filter (10) for syringes. Therefore, it is preferable to limit the silicon content to 0.5 wt % to 1.0 wt %.

The iron used may be powders manufactured by a reduction method or a spraying method, and nickel, molybdenum and chromium powders are alloyed with the iron. However, the state of each ingredient is not limited to this embodiment.

The metal powders may be powders manufactured by a high-pressure water spraying method and have an irregular shape. Also, the metal powders may be composed of 40 to 70% of powders with a particle size of 140 mesh to less than 200 mesh, 20 to 55% of powders with a particle size of 200 mesh to less than 270 mesh, and greater than 0 to 5% of powders with a particle size of 270 mesh or more. Incidentally, it is important to ensure that the metal powders have a Green strength that allows handling after melting the metal ingredients configured as described above, and obtain a filtering power and flow rate suitable for a syringe. Therefore, the metal powders may be alloy powders manufactured by a high-pressure water spraying method, which makes powders of an irregular shape rather a spherical shape. In addition, the metal powders, which have such an irregular shape, allow the metal filter 10 for syringes to have a filtering power capable of filtering out at least 90% of foreign substances with a size of 0.005 mm, and also to have an appropriate particle size such that it takes 25 seconds or less for a syringe to administer a liquid medicine. A molding lubricant may be added to the process of manufacturing the metal filter 10 for syringes. The molding lubricant may be included in an amount of 0.5 to 1.5 parts by weight based on 100 parts by weight of the metal powders. In an embodiment, Kenolube may be used as the molding lubricant. However, the type of the molding lubricant is not limited thereto, and zinc stearate and amide wax may also be used. During molding, metal powders in the mold are compressed to cause friction against the mold surface. At this time, heat may be generated along with scratches on the mold surface.

The molding lubricant is used to prevent these. However, when the amount of the molding lubricant added exceeds 1.5 wt %, the compressibility may be deteriorated, burn-out may occur during sintering, resulting in defects in the molded body, and the molding lubricant may remain in oxidized form on the surface of the metal filter 10 for syringes as a partly manufactured product. On the other hand, when the molding lubricant is used in an amount less than 0.5 wt %, it may cause generation of heat and scratches on the mold surface, which may be unsuitable for use. Therefore, preferably, the molding lubricant is included in an amount of 0.5 to 1.5 parts by weight based on 100 parts by weight of the metal powders.

As described above, the metal filter 10 for syringes, composed of metal powders, is porous so that it can filter the foreign substances contained in a liquid medicine. Also, as described above, when a liquid medicine is administered to a patient, the metal filter 10 for syringes allows to give an injection to the patient promptly while filtering the foreign substances contained in the liquid medicine. Hereinafter, a manufacturing method of the aforementioned metal filter 10 for syringes will be described with reference to the following drawings.

Figure 4:
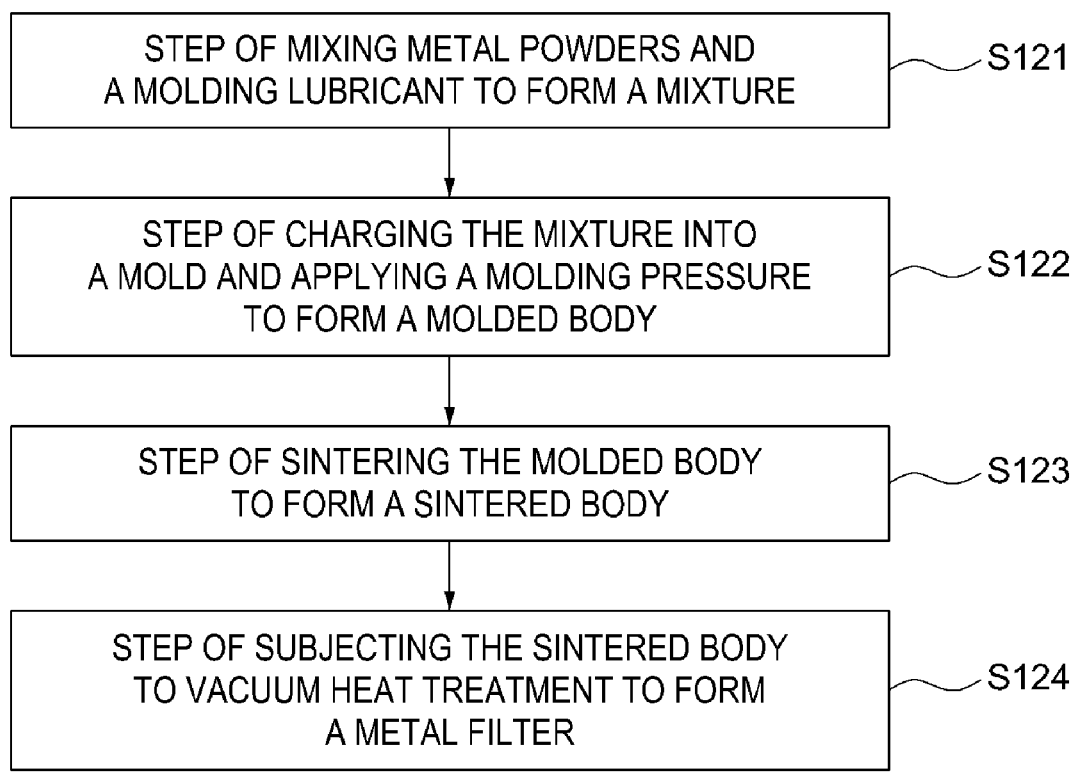
FIG. 4 is a flowchart of a manufacturing method of a metal filter for syringes according to an embodiment of the present invention.

With reference to FIG. 4, the manufacturing method of a metal filter for syringes comprises the step (S121) of mixing metal powders and a molding lubricant to form a mixture. Specifically, the metal powders and molding lubricant in step S121 are the same as described above, and thus, a detailed description thereof will be omitted. The metal powders and molding lubricant configured as described above may be charged into a mixer and mixed therein, and the mixing time may be 15 to 35 minutes.

The manufacturing method of a metal filter for syringes may comprise, after step S121, the step (S122) of charging the mixture into a mold and applying a molding pressure to form a molded body. Specifically, step S122 is a step of charging the mixture formed in step S121 into a mold and applying a molding pressure to form a molded body. Here, the molding pressure may be a pressure of 2 ton/cm$^2$ to 5 ton/cm$^2$. When the pressure is less than 2 ton/cm$^2$, the molded body may not be formed in a predetermined shape, and also the compressed density may decrease, so that the metal filter 10 for syringes may have a larger pore size, resulting in deteriorated filtering performance. On the other hand, when the pressure exceeds 5 ton/cm$^2$, the density of the molded body may increase, so that the porosity may decrease, leading to a problem that the time for administration of a liquid medicine by a syringe becomes longer. Therefore, preferably, the molding pressure is limited to a range of 2 ton/cm$^2$ to 5 ton/cm$^2$. Also, step S122 may further comprise the step of checking for burrs in the molded body and injecting air to remove them.

The manufacturing method of a metal filter for syringes may comprise, after step S122, the step (S123) of sintering the molded body to form a sintered body. Step S123 is a step of applying heat to the molded body to allow sufficient bonding between the particles constituting the molded body and thereby to improve the bonding force between the particles. In particular, the molded body may be sintered at a temperature of 1100° C. to 1200° C. in a gas atmosphere of any one of decomposed ammonia, hydrogen, and a mixed gas of hydrogen and nitrogen for 25 to 45 minutes. When the sintering temperature is less than 1100° C., the sintering temperature is too low to achieve proper sintering. When the sintering temperature exceeds 1120° C., the desired filtering power and flow rate cannot be obtained, and the dimensional precision may decrease, leading to low assembling performance between a syringe and the metal filter 10 for syringes. When the sintering time is less than 20 minutes, sintering is not sufficiently performed, leading to a decreased filtering power. When the sintering time exceeds 45 minutes, the strength increases, but the dimensional precision may be lowered due to sintering deformation.

Also, the step of preheating the molded body may be performed before sintering the molded body at a temperature of 1100° C. to 1200° C. for 25 to 45 minutes in step S123, and also, after sintering, the step of cooling the sintered body in the sintering furnace may be further performed. More specifically, a plurality of molded bodies may be put into one tray, and the tray may be charged into a continuous furnace having a preheating zone, a heating zone, and a cooling zone so that the tray will be passed through the continuous furnace. The tray may be preheated while passing through the preheating zone at a temperature of 400° C. to 900° C. The tray that has passed through the preheating zone may be charged into the continuous furnace at such a rate that the molded bodies can be sintered in the heating zone at a temperature of 1100° C. to 1200° C. for 25 to 45 minutes. Then, the sintered body that has been heated may be cooled in the sintering furnace while passing through a water jacket. Here, the sintered body may be cooled by water cooling. However, the cooling method of the molded body is not limited to the water cooling according to this embodiment.

The manufacturing method of a metal filter for syringes may comprise, after step S123, the step (S124) of subjecting the sintered body to vacuum heat treatment to form a metal filter. Specifically, in step S124, the sintered body may be subjected to vacuum heat treatment at a temperature of 1100° C. to 1200° C. When the sintered body is subjected to vacuum heat treatment at a temperature of less than 1100° C., the strength of the metal filter 10 for syringes may decrease, and also the density of the material may decrease, so that the pore size may become large, leading to deteriorated filtering performance against foreign substances. On the other hand, when the sintered body is subjected to vacuum heat treatment at a temperature exceeding 1200° C., the shape of the metal filter 10 for syringes may be deformed, and in particular, the flow rate may be lowered down due to decreased porosity, leading to low practicability. Therefore, it is preferable that the temperature of the vacuum heat treatment of the sintered body is controlled at a temperature of 1100° C. to 1200° C. Thereafter, the vacuum heat-treated, sintered body may be subjected to gas cooling at a rate of 0.4 to 1.0° C./sec for 20 to 60 minutes to form a metal filter 10 for syringes. Here, the vacuum heat-treated, sintered body may be cooled using nitrogen (N2) gas. However, the cooling method of the vacuum heat-treated, sintered body is not limited to this embodiment.

Here, the heat treatment using vacuum involves a less amount of gases containing impurities such as oxygen, carbon dioxide, and carbon monoxide, and thus prevents a surface reaction such as oxidation and carburization from occurring in the molded body. In addition, it can remove, through thermal decomposition or reduction, contaminants on the surface such as remnants of the molding lubricant used in the process of manufacturing the metal filter 10 for syringes. That is, the metal filter 10 for syringes that went through vacuum heat treatment can prevent transformation of the chemical ingredients of the materials and maintain a clean surface. In addition, the surface of the metal filter 10 for syringes is kept clean even after vacuum heat treatment. Thus, the filter does not require post-treatment after the vacuum heat treatment, and thus is economical.

Also, since the sintered body is subjected to vacuum heat treatment in step S124, it can prevent a chemical reaction between the metal filter 10 for syringes and a liquid medicine even when the liquid medicine is injected into the syringes in advance.

When a liquid medicine is administered to the body of a patient, it is generally preferable that at least 90% of the foreign substances be filtered. The metal filter 10 for syringes manufactured by the aforementioned method is designed to have a uniform pore size and an optimized thickness of the second body 13, and thus can filter at least 90% of the foreign substances contained in a liquid medicine. Also, in particular, the metal filter 10 for syringes formed by the aforementioned method is subjected to vacuum heat treatment so that it will have a density of 5.2 g/cm$^3$ to 5.8 g/cm$^3$. When the density of the metal filter 10 for syringes that has undergone vacuum heat treatment is less than 5.2 g/cm$^3$, the porosity increases, which shortens the time for administering a liquid medicine, but the filtering power may decrease. Conversely, when the density of the metal filter 10 for syringes exceeds 5.8 g/cm$^3$, the filtering power increases, but the time for administering a liquid medicine increases excessively, which is not efficient. Therefore, when the density of the metal filter 10 for syringes is 5.2 g/cm$^3$ to 5.8 g/cm$^3$, the time for administering a liquid medicine is 12 to 25 seconds, and it can filter at least 90% of the foreign substances contained in a liquid medicine, which is most suitable.

Hereinafter, specific experimental examples for step S124 will be described.

Example 3

In Example 3, metal powders composed of, by weight, 0.006% of carbon (C), 0.007% of sulfur (S), 2.4% of molybdenum (Mo), 13.3% of nickel (Ni), 0.1% of manganese (Mn), 16.8% of chromium (Cr), 0.9% of silicon (Si), and the balance of iron (Fe) and 1.0 part by weight of a molding lubricant based on 100 parts by weight of the metal powders were mixed for 25 minutes to form a mixture. A molding pressure of 3 ton/cm$^2$ was applied to the mixture to form a molded body. Then, the molded body was sintered at a temperature of 1140° C. for 35 minutes to form a sintered body. Then, the sintered body was subjected to vacuum heat treatment at 1100° C., followed by cooling using nitrogen gas for 30 minutes to obtain a metal filter.

Example 4

In Example 4, a metal filter was manufactured by controlling the vacuum heat treatment temperature at 1200° C., and keeping the remaining process parameters identical to those of Example 3.

Comparative Example 3

In Comparative Example 3, a metal filter was manufactured by controlling the vacuum heat treatment temperature at 1000° C., and keeping the remaining process parameters identical to those of Example 3.

Comparative Example 4

In Comparative Example 4, a metal filter was manufactured by controlling the vacuum heat treatment temperature at 1250° C., and keeping the remaining process parameters identical to those of Example 3.

Experimental Method

Measurements were made for the time required to administer 10 cc of a liquid medicine at a normal injection pressure after a metal filter is mounted into a syringe, and its filtering power against foreign substances. Here, comparison was made between the foreign substances contained in the liquid medicine in an ampoule and the foreign substances contained in the liquid medicine discharged through the metal filter. The filtering power is the reduction rate of foreign substances expressed in percentage.

TABLE 2

| Classification | Time required (sec) | Filtering power (%) | Corrosion resistance |
| --- | --- | --- | --- |
| Example 3 | 12 | 90 | Conforming |
| Example 4 | 25 | 96 | Conforming |
| Comparative Example 3 | 10 | 82 | Nonconforming |
| Comparative Example 4 | 45 | 99 | Conforming |

As shown in Table 2 above, in Example 3 of the present invention, it took 12 seconds for the syringe to administer the liquid medicine, and the filtering power against foreign substances was 90%. Also, in Example 4, it took 25 seconds for the syringe to administer the liquid medicine, and the filtering power against foreign substances was 98%. That is, it can be understood that as the temperature of the vacuum heat treatment increases, the filtering power against foreign substances increases, and the time required for administration of a liquid medicine increases. Also, it can be seen that the corrosion resistance of Examples 3 and 4 satisfies the criteria and thus is conforming.

In contrast, in Comparative Example 3, although the time required for administration of the liquid medicine was 10 seconds, so that the rate of administration of a liquid medicine was higher than those of Examples 3 and 4, the filtering power was merely 82%, which was lower than those of Examples 3 and 4, and the corrosion resistance did not satisfy the criteria and thus was non-conforming. In addition, although Comparative Example 4 achieved a filtering power of 99%, which was similar to that of Example 4, and satisfied corrosion resistance, the time required for administration of a liquid medicine in Comparative Example 4 was 45 seconds, and thus the rate of administration of a liquid medicine was significantly low. That is, it can be understood that, when the temperature in the vacuum heat treatment process exceeds 1200° C., the increase in the filtering power becomes small, but the pore size becomes too small, so that the time required for the syringe to administer a liquid medicine greatly increases. Also, when the pore size becomes too small, more force should be applied to a syringe if the liquid medicine in the syringe is to be administered to a patient more promptly. This requires an unnecessary amount of force when giving an injection, and thus is impractical.

Therefore, in step S124 of the manufacturing method of a metal filter for syringes, it is preferable to subject the sintered body to vacuum heat treatment at a temperature of 1100° C. to 1200° C. so that the filtering power of the metal filter 10 for syringes is at least 90% and the time for administering a liquid medicine is minimized.

According to an embodiment of the present invention, the titanium filter for syringes manufactured by the manufacturing method of a titanium filter for syringes is manufactured through vacuum sintering, so that intergranular sintering occurs to ensure strength and maintain the excellent corrosion resistance of titanium itself. Thus, it is possible to prevent rusting on the titanium filter resulting from a reaction between the filter and a liquid medicine. That is, the titanium filter for syringes can be safely used.

Also, the use of the titanium filter manufactured by the manufacturing method of a titanium filter for syringes can prevent administration of foreign substances to patients and allows to give an injection to a patient promptly. More specifically, the present invention allows to obtain filtering performance against foreign substances by controlling the process parameters such as pressure and temperature and thereby controlling the rate at which a syringe administers a liquid medicine in an ampoule.

Also, according to an embodiment of the present invention, the metal filter for syringes manufactured by the manufacturing method of a metal filter for syringes is manufactured through vacuum heat treatment, so that it is possible to prevent rusting on the metal filter resulting from a reaction between the filter and a liquid medicine. That is, the metal filter for syringes can be safely used.

Also, the metal filter for syringes manufactured by the manufacturing method of a metal filter for syringes allows a syringe to draw in a liquid medicine rapidly while filtering foreign substances.

It should be understood that the effects of the present invention are not limited to the effects described above, but include all effects that can be deduced from the detailed description of the present invention or the constitution of the invention described in the claims.

The above description of the present invention is provided for the purpose of illustration, and it would be understood by a person skilled in the art that various changes and modifications may be made without changing the technical idea and essential features of the present invention. It is therefore to be understood that the aforementioned embodiments are illustrative in all aspects and not restrictive. For example, each component described to be of a single type can be implemented in a distributed manner. Likewise, components described to be distributed can be implemented in a combined manner.

The scope of the present invention is defined by the appended claims, and all changes or modifications derived from the meaning and scope of the claims and their equivalents should be construed as being included within the scope of the present invention.

What is claimed is:

1. A manufacturing method of a titanium filter for syringes, comprising:
   a) mixing titanium powders and a molding lubricant to form a mixture;
   b) charging the mixture into a mold and applying a molding pressure to form a molded body;
   c) degreasing the molded body under vacuum in a vacuum furnace; and
   d) sintering the molded body, which has been degreased under vacuum, to form a titanium filter,
   wherein, in step a),
   the titanium powders have a composition ratio of square powders:spherical powders of 70 to 90%: 10 to 30%, and
   the titanium powders are a mixture of 37 to 67% of the square powders with a particle size of 75 µm to 150 µm, 14 to 44% of the square powders with a particle size of 0 µm to 75 µm, and 10 to 30% of the spherical powders with a particle size of 0 µm to 75 µm, and
   wherein, in step d),
   the titanium filter is subjected to vacuum heat treatment to have a density of 2.5 g/cm3 of 4.0 g/cm3.

2. The manufacturing method of claim 1,
   wherein, in step a),
   the titanium powders are alloy powders composed of, by weight, 0 to 0.4% of oxygen (O), 0 to 0.04% of nitrogen (N), 0 to 0.03% of hydrogen (H), 0 to 0.04% of carbon (C), 0 to up to 0.05% of chlorine (Cl), 0 to 0.05% of iron (Fe), 0 to 0.03% of silicon (Si) and the balance of titanium (Ti), based on the total weight of the titanium powders.

3. The manufacturing method of claim 1,
   wherein, in step a),
   the molding lubricant is included in an amount of 0.3 to 1.0 part by weight based on 100 parts by weight of the titanium powders.

4. The manufacturing method of claim 1,
   wherein, in step c),
   the molded body is degreased in a vacuum atmosphere in the vacuum furnace at a temperature of 300° C. to 700° C. under a degree of vacuum of $10^{-2}$ Torr or less for 20 to 60 minutes.

5. The manufacturing method of claim 1,
   wherein, in step d),
   the molded body is sintered under vacuum at a temperature of 1120° C. to 1160° C. for 30 to 60 minutes.

6. The manufacturing method of claim 5,
   wherein, in step d),
   the molded body is sintered under vacuum at a vacuum pressure of $10^{-3}$ Torr to $10^{-6}$ Torr.

* * * * *